(12) United States Patent
Holladay et al.

(10) Patent No.: US 7,649,099 B2
(45) Date of Patent: Jan. 19, 2010

(54) METHOD OF FORMING A DIANHYDROSUGAR ALCOHOL

(75) Inventors: Johnathan E. Holladay, Kennewick, WA (US); Jianli Hu, Kennewick, WA (US); Yong Wang, Richland, WA (US); Todd A. Werpy, West Richland, WA (US); Xinjie Zhang, Burlington, MA (US)

(73) Assignee: Battelle Memorial Institute, Richland, WA (US)

( * ) Notice: Subject to any disclaimer, the term of this patent is extended or adjusted under 35 U.S.C. 154(b) by 521 days.

(21) Appl. No.: 11/341,961

(22) Filed: Jan. 26, 2006

(65) Prior Publication Data

US 2007/0173652 A1 Jul. 26, 2007

(51) Int. Cl.
*C07C 29/00* (2006.01)
*C07D 315/00* (2006.01)
*C07D 493/00* (2006.01)
*C07H 1/00* (2006.01)
*C07H 17/00* (2006.01)
*C07H 5/04* (2006.01)
*C07H 1/06* (2006.01)
*C13K 5/00* (2006.01)

(52) U.S. Cl. ............ 549/464; 536/18.5; 536/18.6; 536/55.3; 536/123.1; 536/124; 536/126; 549/417; 568/902

(58) Field of Classification Search ............ 536/18.5, 536/18.6, 18.7, 55.3, 123.1, 124, 126; 549/417, 549/464; 568/902
See application file for complete search history.

(56) References Cited

U.S. PATENT DOCUMENTS

| 3,160,641 | A | 12/1964 | Hartmann et al. |
| 4,297,290 | A | 10/1981 | Stockburger |
| 4,408,061 | A | 10/1983 | Salzburg et al. |

(Continued)

FOREIGN PATENT DOCUMENTS

CA 1178288 11/1984

(Continued)

OTHER PUBLICATIONS

Fleche, et al., "Isosorbide" Starch/Starke, vol. 38, 1986, pp. 26-30.

(Continued)

*Primary Examiner*—Taylor Victor Oh
(74) *Attorney, Agent, or Firm*—Wells St. John P.S.

(57) ABSTRACT

The invention includes methods of producing dianhydrosugars. A polyol is reacted in the presence of a first catalyst to form a monocyclic sugar. The monocyclic sugar is transferred to a second reactor where it is converted to a dianhydrosugar alcohol in the presence of a second catalyst. The invention includes a process of forming isosorbide. An initial reaction is conducted at a first temperature in the presence of a solid acid catalyst. The initial reaction involves reacting sorbitol to produce 1,4-sorbitan, 3,6-sorbitan, 2,5-mannitan and 2,5-iditan. Utilizing a second temperature, the 1,4-sorbitan and 3,6-sorbitan are converted to isosorbide. The invention includes a method of purifying isosorbide from a mixture containing isosorbide and at least one additional component. A first distillation removes a first portion of the isosorbide from the mixture. A second distillation is then conducted at a higher temperature to remove a second portion of isosorbide from the mixture.

24 Claims, 5 Drawing Sheets

U.S. PATENT DOCUMENTS

| | | | |
|---|---|---|---|
| 4,506,086 A | 3/1985 | Salzburg et al. | |
| 4,564,692 A | 1/1986 | Feldmann et al. | |
| 4,861,513 A | 8/1989 | Lueders et al. | |
| 5,093,535 A | 3/1992 | Harrison et al. | |
| 6,013,812 A * | 1/2000 | Haas et al. | 549/416 |
| 6,124,443 A | 9/2000 | Darsow | |
| 6,392,062 B1 | 5/2002 | Haas | |
| 6,407,266 B2 | 6/2002 | Bhatia | |
| 6,639,067 B1 | 10/2003 | Brinegar et al. | |
| 6,689,892 B2 | 2/2004 | Andrews et al. | |
| 6,693,209 B2 | 2/2004 | Van Es et al. | |
| 7,439,352 B2 * | 10/2008 | Moore et al. | 536/124 |
| 2002/0052516 A1 | 5/2002 | Moore et al. | |
| 2003/0097028 A1 | 5/2003 | Fuertes | |
| 2003/0229235 A1 | 12/2003 | Bhatia | |
| 2004/0030161 A1 | 2/2004 | Bhatia | |
| 2004/0110969 A1 | 6/2004 | Fleche et al. | |
| 2004/0110994 A1 | 6/2004 | Bhatia | |

FOREIGN PATENT DOCUMENTS

| | | |
|---|---|---|
| EP | 0061055 A1 | 9/1982 |
| EP | 0201067 A2 | 11/1986 |
| EP | 0380402 A1 | 8/1990 |
| EP | 0915091 A2 | 5/1999 |
| EP | 1179535 A1 | 2/2002 |
| EP | 1179536 A1 | 2/2002 |
| WO | 9721697 A1 | 6/1997 |
| WO | 0014081 A1 | 3/2000 |
| WO | 0041985 | 7/2000 |
| WO | 0172136 A1 | 10/2001 |
| WO | 0194352 A1 | 12/2001 |
| WO | 0239957 A2 | 5/2002 |
| WO | 03022064 A1 | 3/2003 |
| WO | 03089436 A1 | 10/2003 |
| WO | 03089445 A1 | 10/2003 |
| WO | 2005047228 A1 | 5/2005 |

OTHER PUBLICATIONS

2006 Chemical Abstracts Catalog, published 2006 by Chemical Abstracts Service. p. 52.

* cited by examiner

METHOD OF FORMING A DIANHYDROSUGAR ALCOHOL

GOVERNMENT RIGHTS

The invention was made with Government support under Contract DE-AC0676RLO 1830, awarded by the U.S. Department of Energy. The Government has certain rights in the invention.

TECHNICAL FIELD

The invention pertains to a process for production of dianhydrosugar alcohols, a process of forming a sugar product, methods of forming isosorbide and methods of purifying isosorbide.

BACKGROUND OF THE INVENTION

Anhydrosugars, dianhydrosugar alcohols and their derivatives are commercially valuable for a variety of applications including therapeutic uses and use as copolymers to improve properties of polymer materials. Conventional production of dianhydrosugar alcohols such as isosorbide can be expensive and inefficient. Additionally, conventional processes can be environmentally unfriendly.

It is desirable to develop alternative methods for producing anhydro and dianhydrosugar alcohols.

SUMMARY OF THE INVENTION

In one aspect the invention encompasses a method of producing a dianhydrosugar alcohol. In a first reactor, a polyol is reacted in the presence of a first catalyst to form a monocyclic sugar. The monocyclic sugar is transferred to a second reactor where it is converted to a dianhydrosugar alcohol in the presence of a second catalyst.

In one aspect the invention encompasses a process of forming isosorbide. Within a first reactor, an initial reaction is conducted at a first temperature in the presence of a solid acid catalyst. The initial reaction involves reacting sorbitol to produce initial products which can include 1,4-sorbitan, 3,6-sorbitan, 2,5-mannitan and 2,5-iditan. The initial products are transferred to a second vessel where, utilizing a second temperature, the 1,4-sorbitan and 3,6-sorbitan are converted to isosorbide.

In one aspect the invention encompasses a method of purifying isosorbide. A mixture containing isosorbide and at least one additional component is distilled at a first distillation temperature. This first distillation removes a first portion of the isosorbide from the mixture. A second distillation is then conducted at a second temperature which is higher that the temperature of the first distillation. The second distillation removes a second portion of isosorbide from the mixture.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

Figure 1:
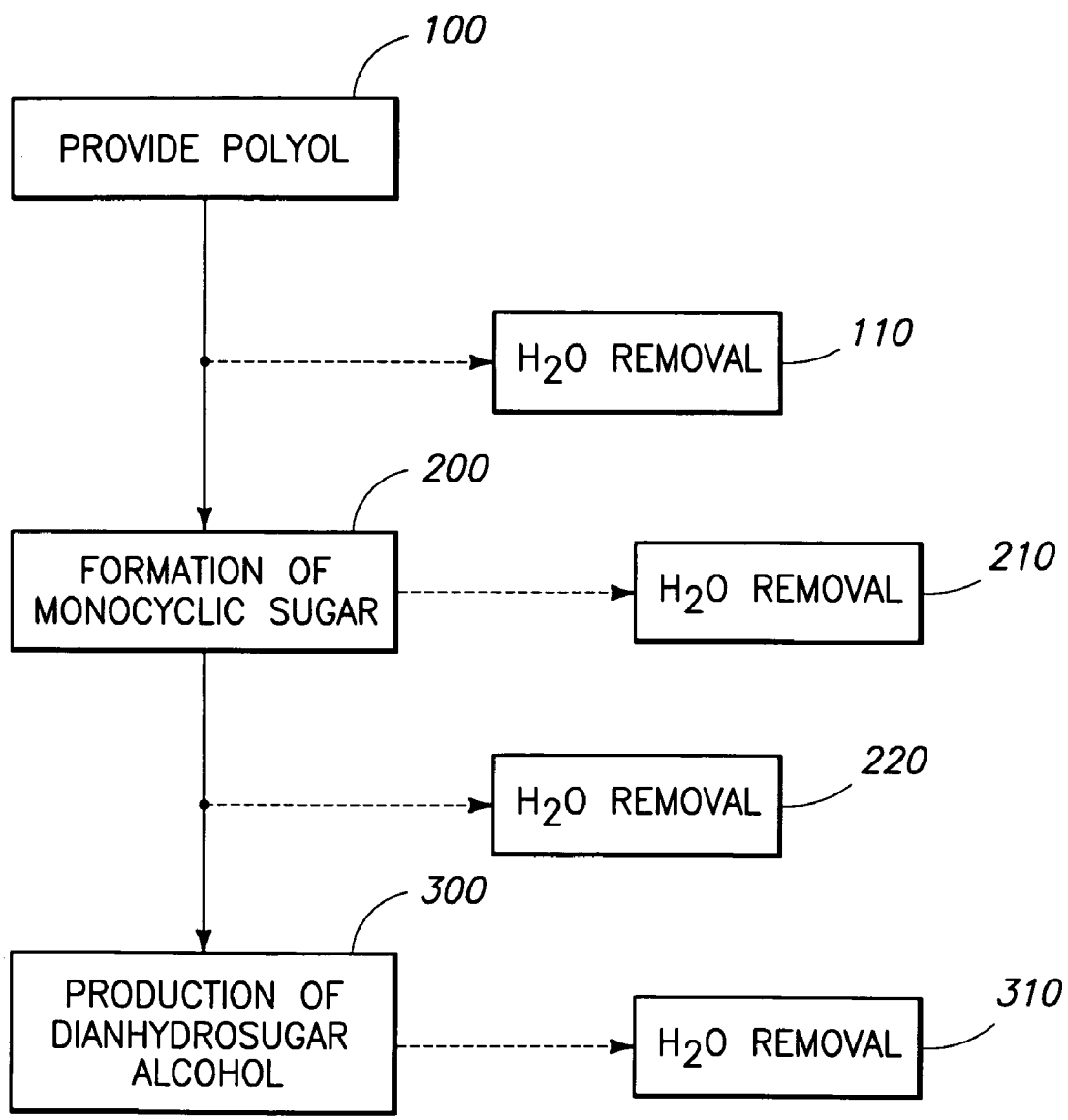
FIG. 1 is a flowchart diagram depicting methodology and processing in accordance with one aspect of the invention.

This disclosure of the invention is submitted in furtherance of the constitutional purposes of the U.S. Patent Laws "to promote the progress of science and useful arts" (Article 1, Section 8).

In general, methods according to the present invention can be utilized to produce dianhydrosugar alcohols from various polyols. Exemplary dianhydrosugar alcohols that can be produced utilizing methods of the invention include but are not limited to sugars having a formula (I).

Formula (I):

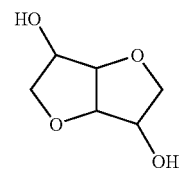

Although the invention is described with reference to production of such compounds, it is to be understood that the methodology described can be equally useful for production of alternative dianhydrosugar products.

Formation of dianhydrosugar alcohols according to methods of the present invention can typically comprise a two step reaction process. An exemplary two step reaction process in accordance with the invention is set forth generally in FIG. 1. As illustrated, a polyol can be provided in a pre-reaction stage 100. The polyol can be utilized as an initial compound for conducting a first step of a reaction in a first stage 200 of the reaction process. The polyol provided in pre-reaction stage 100 is not limited to a specific length or any specific hydroxyl group content. In some implementations of the present invention, the polyol provided can preferably be a polyol or a mixture of polyols having formula (II).

Formula (II):

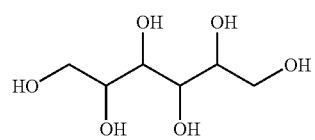

Alternative polyols, including those having fewer or additional carbon atoms relative to formula (II), can be utilized where alternative mono and/or dianhydro-products are desired.

In first reaction stage 200, the initial compound can undergo a first reaction step in the presence of a dehydration catalyst to form at least one corresponding monocyclic sugar. Where the initial compound is a polyol of formula (II), the monocyclic sugar can be one or more anhydrosugar alcohols having a formula (III).

Formula (III):

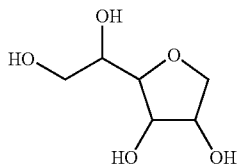

The catalyst of stage 200 is not limited to a particular catalyst. Exemplary dehydration catalysts which can be used in monocyclic sugar formation stage 200 include but are not limited to a solid acid catalyst such as a heteropoly acid, an anion exchange resin, an acidic clay, a molecular sieve type material, a sulfated zirconia, mineral acids (e.g. sulfuric acid, phosphoric acid, hydrochloric acid), and mixtures thereof.

The monocyclic sugar formation is preferably conducted under mild temperature conditions. An appropriate temperature can depend upon factors such as the starting polyol(s) utilized, the catalyst utilized, and the reaction pressure. In particular implementations, monocyclic sugar formation can be performed at a temperature of from about 70° C. to about 120° C., and more preferably at a temperature of from 90° C. to about 115° C. It can be advantageous to conduct the monocyclic sugar formation step of the reaction under mild conditions to enhance the selectivity of the reaction step. Where the initial compound has formula (II), conducting monocyclic sugar formation within the preferred temperature range can increase selective production of compounds having formula (III) relative to byproducts having a formula (IV).

Formula (IV):

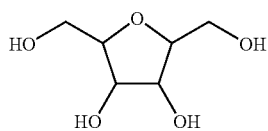

In addition to the above benefits of conducting monocyclic sugar formation under mild conditions, the preferred temperature range can also minimize oligomer and/or polymer formation. Oligomers and/or polymers formed during the reaction can potentially foul certain solid catalysts. It can be beneficial to minimize formation of such oligomers and polymers to minimize fouling and thereby allow efficient utilization of the solid acid catalyst during the monocyclic sugar formation. The use of solid catalysts can allow stage 200 of FIG. 1 to be conducted continuously without a need for subsequent separation of the acid for disposal or purification purposes. It is to be understood however that the invention encompasses both continuous and batch-wise processes.

Formation of monocyclic sugars in stage 200 can be conducted in the presence of water. Where water is present during monocyclic sugar formation, the initial polyol can be provided in aqueous solution containing from about 30% to about 70% of the polyol compound by weight. Alternatively, the monocyclic sugar formation can be initiated in an absence of water (discussed below). It can be advantageous in some instances to conduct monocyclic sugar formation in the presence of water since increased selectivity toward production of formula (III) compounds relative to formula (IV) byproducts can occur when water is present. In particular aspects, a ratio of formula (III) compounds relative to formula (IV) byproducts can be greater than or equal to about 8:1. Preferably such ratio is at least about 10:1.

In some aspects, monocyclic sugar formation can be conducted in an absence of solvent (neat), or can be conducted utilizing a high-boiling point solvent such as sulfolane. It can be advantageous to utilize a high-boiling point solvent to allow further reduction of the reaction temperature which can further enhance selectivity.

The monocyclic sugars of formula (III) can be converted to corresponding dianhydro alcohol in a second process stage 300 as depicted in FIG. 1. In some implementations, the catalyst utilized during formation of monocyclic sugars can remain in the reaction during production of dianhydrosugar alcohols. However, it can be preferable in some instances to separate the formula (III) products of the monocyclic sugar formation stage from the presence of the stage 200 catalyst utilized, prior to conversion to dianhydrosugar in stage 300. Removal of the formula (III) product from the presence of the catalyst used in reaction stage 200 can be performed during the formation of monocyclic sugars by removal from the stage 200 reactor when the initial amount of the polyol provided to stage 200 of the reaction is depleted by between 50% and 100%. Preferably the removal is performed when the depletion of the polyol reaches from about 80% to about 95%. It can be preferable to perform the removal at from about 90% to about 95% of polyol depletion to maximize conversion to products while minimizing or preventing oligomer and/or polymer formation.

Removal of the formula (III) compounds from the presence of the catalysts used in stage 200 can comprise filtering and/or transferring the monocyclic intermediates to a second reaction vessel. Optionally, the monocyclic intermediates having formula (III) can be collected and purified or isolated from monocyclic byproducts of formula (IV) and other impurities present in reaction stage 200. It is to be understood however that production of dianhydrosugar alcohols in stage 300 can be conducted without prior purification of the formula (III) intermediates.

Stage 300 can comprise dehydration of one or more monocyclic anhydrosugar alcohols produced in stage 200. The dehydration reaction in stage 300 can produce one or more dianhydrosugar alcohols. In some instances the dehydration can produce a single stereoisomer and can be especially useful for producing a desired stereoisomer having formula (I).

Dianhydro alcohol production stage 300 can preferably be conducted at a temperature exceeding the temperature utilized in stage 200. It can be advantageous to perform the dehydration at an elevated temperature to enhance the rate of the dehydration reaction. Accordingly, at a reaction pressure of about 10 mmHg, stage 300 of the reaction can utilize a temperature of greater than or equal to about 120° C. A preferable reaction temperature can be from about 120° C. to about 200° C., and more preferably from about 120° C. to about 140° C. As set forth above with respect to stage 200, the appropriate reaction temperature can vary from the indicated values depending upon factors such as the polyol utilized, the presence and type of catalyst, and the reaction pressure.

Stage 300 can be performed in the presence or absence of an added catalyst. In particular embodiments where a catalyst is utilized, the catalyst can preferably be a mineral acid catalyst such as sulfuric acid, phosphoric acid, hydrochloric acid, p-toluenesulfonic acid, an organic acid, or mixtures thereof. It can be preferable to utilize a non-solid acid catalyst during formation of dianhydrosugar alcohols in stage 300 since oligomer and/or polymer formation during the dehydration can result in fouling of certain solid acid catalysts. However, it is to be understood that a solid acid catalyst can be utilized in stage 300, especially where the dianhydro product is removed from the reaction as it is formed to minimize or prevent formation of oligomers and/or polymers. Minimization of polymerization can advantageously increase overall product yield.

Production of the dianhydrosugar alcohol in stage 300 can optionally be conducted utilizing a high-boiling solvent such as sulfolane, or can be conducted in the presence of a solvent capable of selectively dissolving the dianhydro product relative to one or more of the initial polyol, the reaction intermediates, and byproducts. For example, where the dianhydro product is isosorbide, a solvent such as xylene can be utilized to selectively dissolve isosorbide relative to sorbitol and sorbitan.

The production of dianhydrosugar alcohol in stage 300 can optionally be performed in the presence of added hydrogen and a co-catalyst. An exemplary co-catalyst can comprise a metal on a carbon support. The hydrogen pressure utilized in dehydration step 300 is not limited to a particular value and can comprise, for example, from about 1,000 psi to about 5 psi. Where added hydrogen is utilized, it can be preferable to provide the hydrogen at a pressure of about 30 psi since this hydrogen pressure can allow decreased oligomer formation relative to an absence of hydrogen while also allowing water to be removed during the reaction.

A proposed mechanism by which the presence of hydrogen decreases catalyst fouling is by reduction of aldehyde or other unsaturation to thereby prevent or decrease oligomer formation that occurs in the absence of added hydrogen. This proposed mechanism is supported by the observation that discoloration of the reaction which occurs in an absence of added hydrogen is decreased or eliminated when hydrogen is provided during the dehydration to form dianhydrosugar alcohol. The ability of the added hydrogen to decrease the amount of unsaturation can also result in fewer intermolecular interactions which may allow improved recovery of dianhydrosugar alcohol product during subsequent distillation (discussed below). Although proposed mechanisms for the effects of hydrogen are presented, the proposal of such mechanisms is not intended to in any way limit the scope of the disclosed invention or the claims that follow.

The reaction process of the present invention can include one or more water removal steps 110, 210, 220 and 310. As depicted in FIG. 1, a water removal step 110 can optionally be performed prior to initiation of reaction stage 200. An optional water removal 210 can be conducted during the formation of monocyclic sugars in stage 200. An optional water removal step 220 can be included between stage 200 and the dehydration stage 300. Water removal step 310 can be conducted during the dehydration stage 300. The overall process shown in FIG. 1 can include any combination of water removal steps 110, 210, 220 and 310, or can omit any or all of such optional water removal steps. Where the reaction process includes a water removal step 210 and/or water removal step 300, such water removal can comprise conducting the corresponding reaction step under vacuum.

Water removal step 110 where utilized, can comprise evaporation utilizing conventional methods. It can be advantageous to remove water from the initial polyol material since the rate of conversion to monocyclic sugars is enhanced in the absence of water. The rate can further be enhanced by removal of water during the formation of monocyclic sugars in stage 200 (water removal step 210) in addition to water removal step 110 since water is produced during the formation of monocyclic sugars. Additionally, the presence of water can decrease the life of the stage 200 catalyst.

It can also be beneficial to remove water prior to the dehydration (water removal step 220) and/or during the production of dianhydrosugar alcohols in stage 300 (water removal step 310) since water removal can enhance the rate of conversion from the anhydro formula (III) intermediate(s) to the dianhydro product(s). In addition to enhancing the rate of conversion in stage 300, water removal can allow dehydration to be conducted at decreased temperature relative to the reaction performed in the presence of water.

Methodology of the present invention can include collection of the dianhydrosugar alcohol product from stage 300. Product collection can be performed upon completion of the reaction or alternatively can be performed as the dianhydrosugar alcohol is formed. As discussed above, it can be advantageous to remove the dianhydro product as it is formed to minimize oligomer and polymer formation. Exemplary techniques which can be utilized for removal of the dianhydro alcohol product as it is being formed include, but are not limited to, reactive distillation and steam distillation.

Dianhydrosugar alcohols produced by methods of the present invention can optionally be purified. Purification of the dianhydro product can comprise one or more of crystallization, distillation, recrystallization and washing. Alternatively or in addition to conventional methods, a two step distillation can be performed. The two step distillation can comprise a first distillation step conducted at a first temperature and a second distillation step conducted at a second distillation temperature. Appropriate distillation temperatures will depend upon factors such as the specific dianhydro product being purified and the distillation pressure.

During a first step of the two step distillation procedure, a first portion of the dianhydro product can be collected by conducting the distillation reaction at a temperature sufficient to cause distillation of dianhydro product to occur. The first step of the distillation can be conducted for a length of time sufficient to complete recovery of an amount of product distillable at the first temperature. The completion of distillation step 1 can be determined when no additional product is recovered at the first temperature (which can be accompanied and detected by a decrease in temperature of a distillation reactor due to removal of product distillable at the first temperature).

The second distillation can be performed at a temperature that is higher than the first distillation temperature. It can be advantageous to include the second distillation step at the second temperature to collect a second portion of the dianhydrosugar alcohol product that was not distillable at the first temperature. The two step distillation purification can result in an increased overall product yield which in some instances can be a molar product yield increase of 10% or higher.

Exemplary processing utilizing methods of the present invention is discussed below with reference to production of isosorbide as an exemplary product. It is to be recognized that the invention encompasses production of isosorbide and other dianhydrosugar alcohols as set forth above.

Utilizing methods of the present invention, sorbitol can be reacted in a first vessel to form monocyclic sugars which can include 1,4-sorbitan, 3,6-sorbitan, 2,5-iditan and 2,5-mannitan. With reference to FIG. 1 the sorbitol reaction in the formation of monocyclic sugar stage 200 can preferably comprise a temperature of between 90° C. and 120° C., more preferably about 110° C. It can be advantageous to utilize these mild temperature conditions since this range of temperatures promotes selective production of the 1,4-sorbitan and 3,6-sorbitan intermediates relative to the production of 2,5-iditan and 2,5-mannitan byproducts. The 2,5-iditan and 2,5-mannitan monocyclic sugars are referred to herein as byproducts due to their inability to convert directly to the isosorbide product. Accordingly it is advantageous to maximize production of the 1,4-sorbitan and 3,6-sorbitan intermediates relative to these byproducts to increase the overall isosorbide product yield.

The sorbitol can be provided to reaction stage 200 in aqueous solution, in the presence of one or more additional or alternative solvents, or neat. Where the sorbitol is provided in aqueous solution, the solution can comprise from about 30% to about 70% sorbitol. The sorbitol can be provided to a first reaction vessel and can be dehydrated in the presence of a dehydration catalyst to form at least one of the monocyclic intermediates, which can be accompanied by one or more of the monocyclic byproducts.

Appropriate catalysts for conversion of the sorbitol to the monocyclic sugars include but are not limited to soluble acids such as mineral acids, and solid acid catalysts such as heteropoly acids, anion exchange resins, acidic clays, molecular sieve type materials and sulfated zirconia. As discussed above it can be preferable that the catalysts in stage 200 comprise a solid acid catalyst to allow a continuous reaction without a continuous flow of catalyst.

As discussed above it can be advantageous to remove water prior to and/or during the conversion of sorbitol to the monocyclic sugars. Accordingly, it can be beneficial to conduct stage 200 of the reaction under vacuum.

Upon conversion of at least about 50% of the initial amount of sorbitol provided to the reaction, and preferably upon sorbitol conversion of from about 90% to about 95%, the produced monocyclic sugars can be removed from the presence of the catalyst utilized during stage 200. Such removal can comprise, for example, filtering to remove the catalyst and/or transferring the monocyclic sugars to a second vessel.

Stage 300 of the reaction can comprise dehydration of the monocyclic intermediates 1,4-sorbitan and 3,6-sorbitan to form isosorbide. An optional water removal step 220 can be performed prior to initiation of the dehydration stage 300 to enhance the rate of the dehydration. Additionally or alternatively, the rate of dehydration in stage 300 can be enhanced by one or more of providing vacuum, providing hydrogen, providing a catalyst, and increasing the temperature of the reaction relative to stage 200. Reaction stage 300 can be performed utilizing reactive distillation in the presence of a solid acid catalyst and can optionally comprise steam distillation. It can be advantageous to remove isosorbide from the reaction vessel as it is being formed to inhibit or prevent formation of oligomers and polymers, prevent catalyst fouling and increase yield of the isosorbide product.

The two step process of the present invention can be advantageous relative to single step process formation of isosorbide from sorbitol due to improved yields obtainable by the 2 step process. The isosorbide product yield utilizing the two step process disclosed herein can be as much as about 10% higher than yields obtained utilizing conventional techniques. Additionally, the two step process can allow shorter overall reaction times relative to conventional processes.

It is noted that the process of forming isosorbide as an example of the methods of the present invention produces a single dianhydrosugar alcohol. It is to be understood that the number of dianhydrosugar alcohols and the number of intermediates and byproducts formed during the overall two step reaction will vary depending upon the initial compound and stereochemistry thereof. Where a mixture of polyols and/or stereoisomers is utilized in the formation of monocyclic sugar stage 200, the product can contain a corresponding mixture of dianhydrosugar alcohols.

Isosorbide produced utilizing methods of the present invention can be purified using conventional purification techniques including but not limited to distillation, crystallization, washing, and recrystallization. Alternatively or in addition to the conventional purification techniques, a two step distillation reaction can be utilized to purify the isosorbide. It is to be understood that the disclosed two step distillation can be utilized to collect and/or purify isosorbide or other anhydrosugar alcohols produced by alternative methods.

The two step distillation of isosorbide according to methods of the present invention can comprise an initial distillation performed at a first temperature. The first temperature can preferably be about 150° C. at a reaction pressure of about 10 mmHg. The initial distillation can result in isolation of isosorbide product having about 99% purity or greater. The first distillation can result in an isosorbide molar yield of about 60% or greater relative to the initial amount of sorbitol provided to the reaction process of the invention.

Upon completion of the first distillation step, (which can be detectable by a decrease in the temperature of the distillation reactor utilized), a second distillation step can be performed at a second temperature. The second temperature can preferably be about 170° C. at a distillation pressure of about 10 mmHg. The second distillation step can isolate an additional portion of isosorbide which can typically be approximately 10% or greater molar yield relative to the initial amount of sorbitol provided to the reaction. The second portion of isosorbide collected during the second distillation step can typically have a purity of about 96% or greater.

If additional product purity is desired, the two portions of distilled isosorbide can be individually cooled to form crystals which can be washed with a solvent such as, for example, acetone to remove at least some of impurities present in the distilled portions. Alternatively, the portions can be combined prior to or after cooling, and the resulting crystallized product can be washed. The crystallized isosorbide can optionally be recrystallized to further increase purity using, for example, acetone or other appropriate solvent.

EXAMPLE 1

Acid Catalyzed Conversion of Sorbitol to Isosorbide

Reaction A: In a flask, 50 grams (g) of sorbitol was heated to a temperature of about 135° C. Sulfuric acid (0.5 g) was added. The reaction was conducted for about 2.5 hours with stirring, at a temperature of about 135° C. and a pressure of about 70 mmHg. The flask was then removed from heat and vacuum. Analysis by HPLC indicated a molar yield of isosorbide relative to the starting sorbitol of about 75%.

Reaction B: A mixture containing 50 g of sorbitol and 5 g of water was heated to a temperature of about 90° C. Vacuum was then applied (to about 10 mmHg) to remove water from the mixture. Subsequently, sulfuric acid (0.5 g) was added and the pressure was returned to about 10 mmHg. The reaction was stirred for 10 hours at 90° C. at a pressure of about 10 mmHg, after which time approximately 95% of the sorbitol had been depleted. The reaction temperature was then increased to 100° C. for a period of 8 hours. The reaction was then removed from heat and vacuum. Analysis by HPLC indicated a molar yield of isosorbide relative to the starting sorbitol of about 85%.

Reaction C: Sorbitol (50 g) was heated to about 110° C. Sulfuric acid (0.5 g) was added and vacuum was applied to about 10 mmHg. The reaction was conducted at 110° C., 10 mmHg with stirring for 1 hour. The reaction temperature was then increased over a period of about 10 minutes to a final temperature of about 130° C., and was maintained at 130° C.

for an additional 80 minutes. The reaction was then removed from vacuum and heat. Analysis by HPLC indicated a molar yield of isosorbide relative to the starting sorbitol of about 80%.

Figure 2:
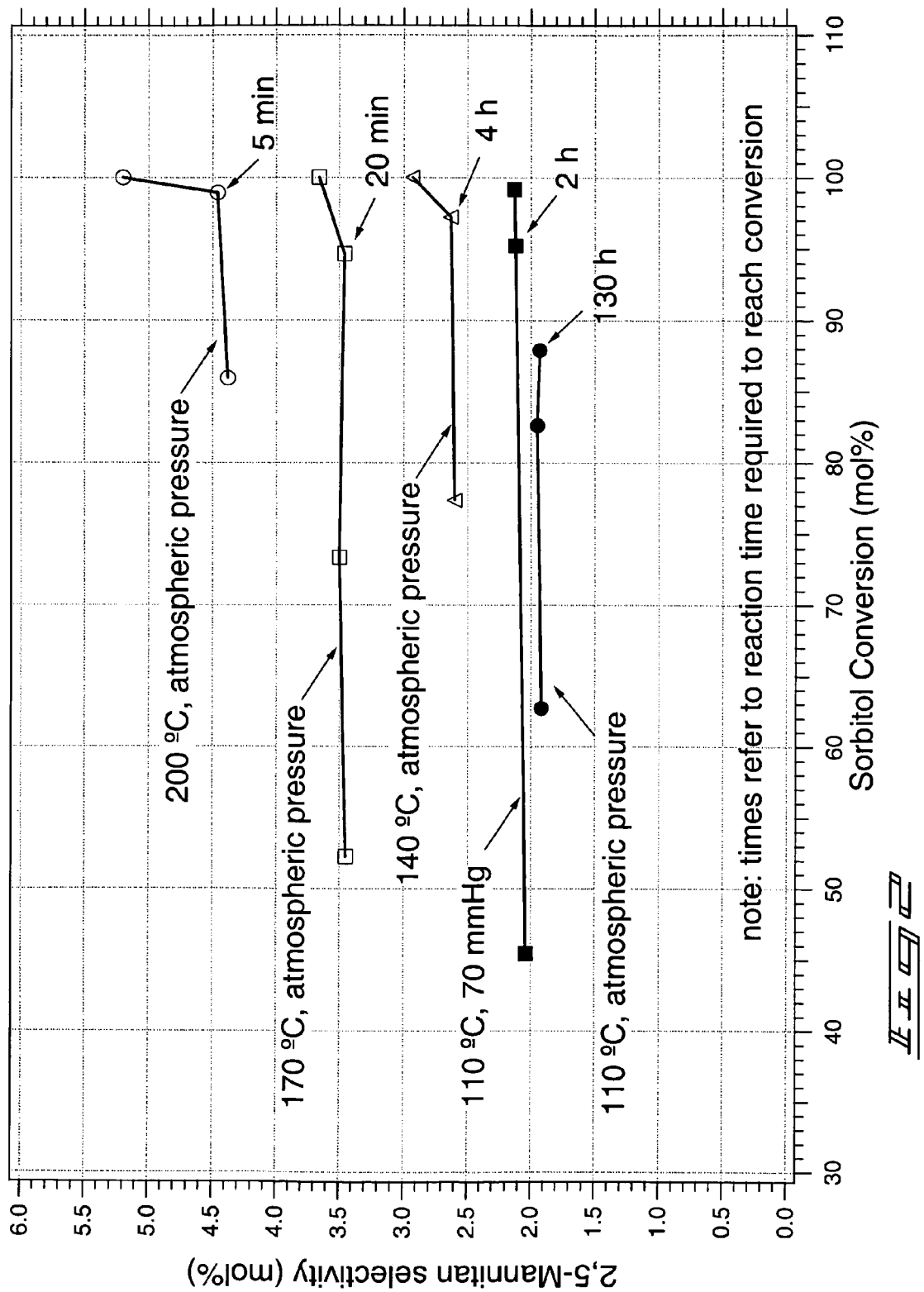
FIG. 2 shows the influence of temperature on byproduct formation.
Figure 3:
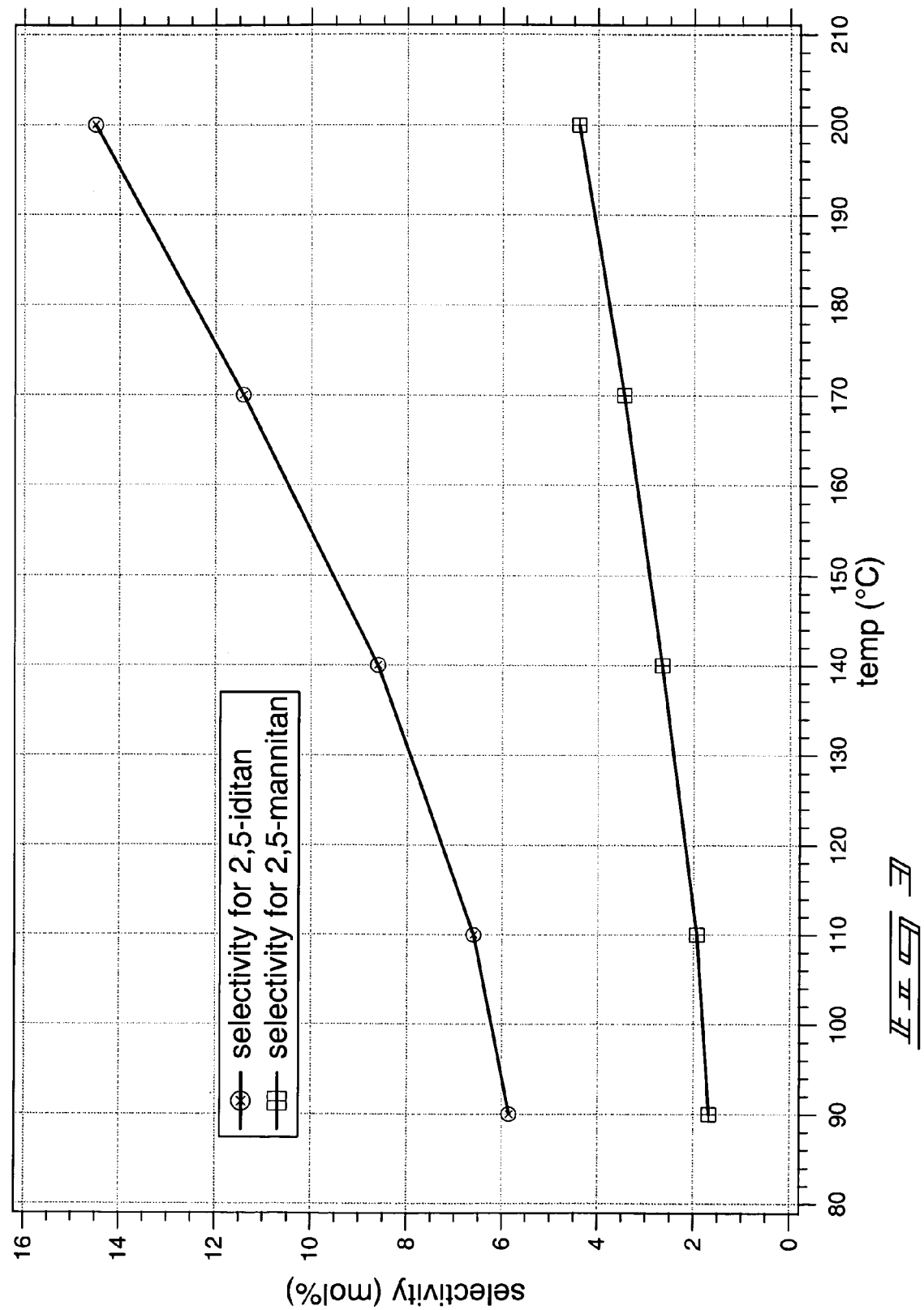
FIG. 3 shows the influence of temperature on selectivity of byproduct formation.
Figure 4:
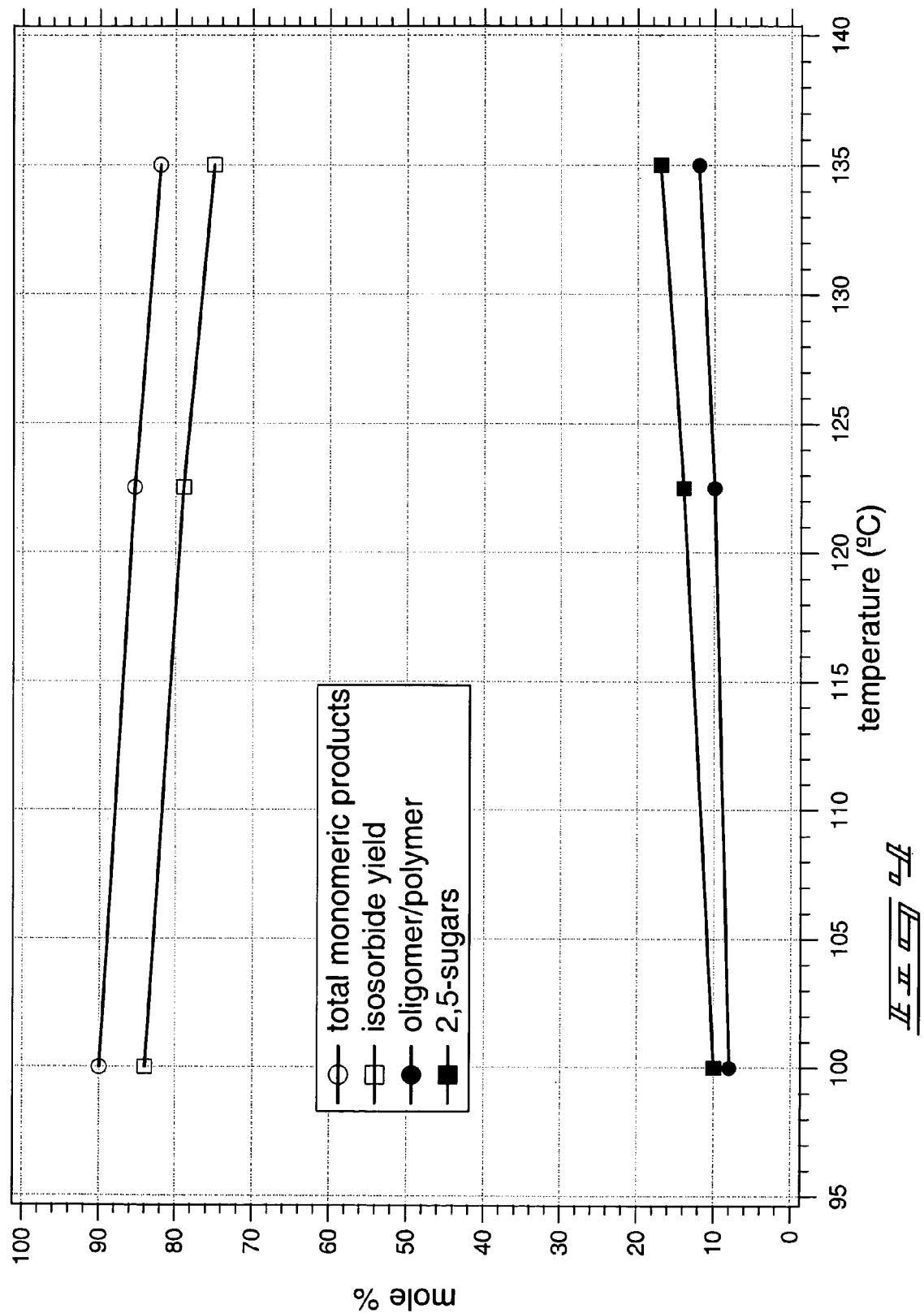
FIG. 4 shows the effect of temperature on formation of oligomeric material.

Comparison between the above reactions and similar reactions at various temperatures with respect to 2,5-anhydrosugar formation is presented in FIGS. 2 and 3. The results show that increased reaction temperature contributes to 2,5-byproduct formation. With reference to FIG. 4, high temperature also contributes to formation of oligomeric or polymeric byproducts. Lowering the reaction temperature from 130° C. to 110° C. produces an increase in isosorbide molar yield from 75% to 85%.

Figure 5:
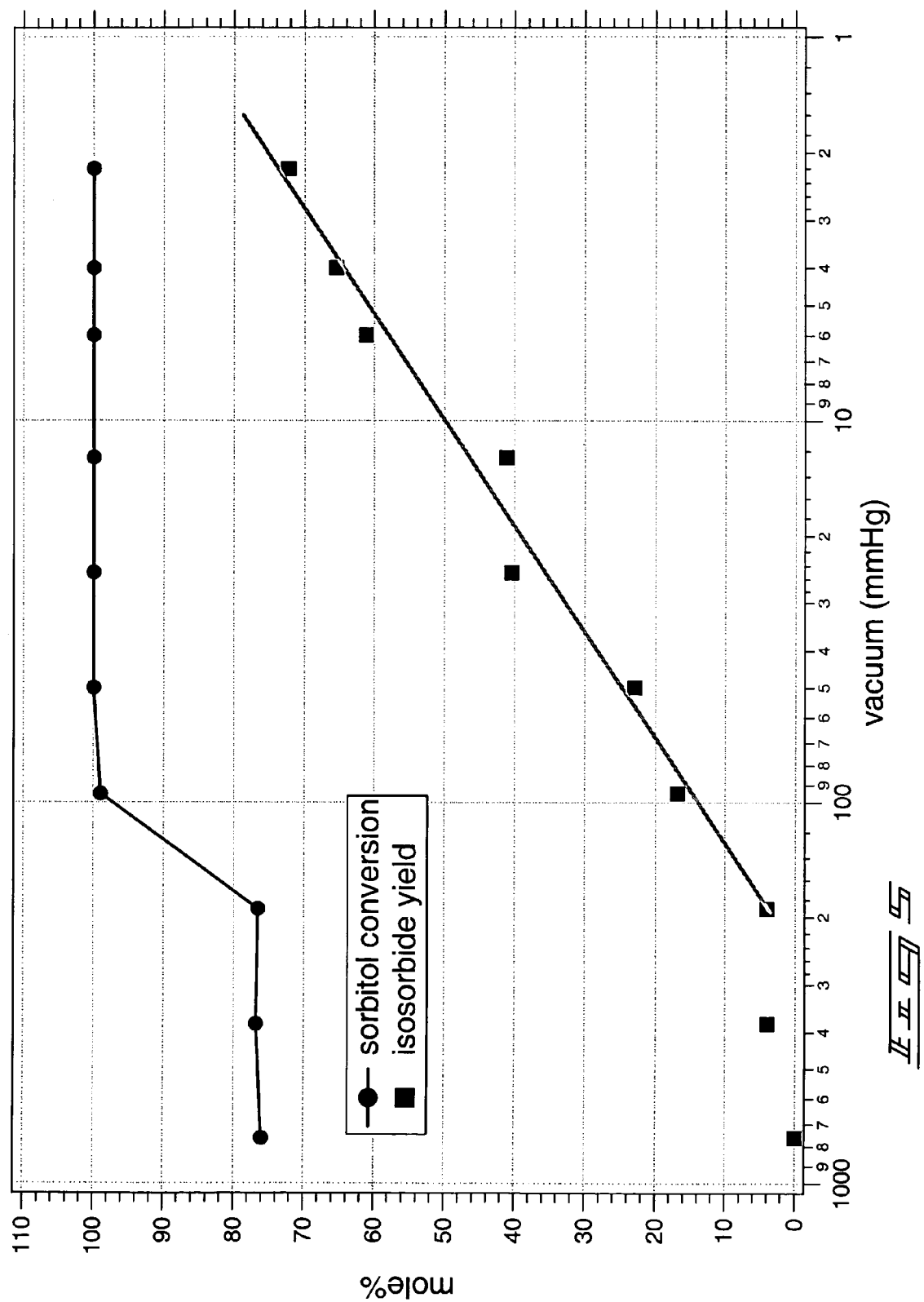
FIG. 5 shows the influence of vacuum on reaction rate at a reaction temperature of 110° C.

An increase in vacuum can be utilized to improve reaction rate for lower temperature reactions. The influence of vacuum on the reaction rate at a temperature of 110° C. is shown in FIG. 5. Since increased vacuum can add to production costs, a two stage process can be advantageous allowing increased vacuum to be utilized over less than an entirety of the reaction process. For example, relatively high vacuum can be utilized during the first step (formation of monocyclic sugars) while an increase in temperature and decrease vacuum is utilized during the second step (production of dianhydrosugar alcohols).

EXAMPLE 2

Production and Two Step Distillation of Isosorbide

Sorbitol (1018 g, 5.590 mol) was heated a reaction vessel to a temperature of about 120° C. reacted in the presence of approximately 120 g of AMBERLYST® 35 catalyst (Rohm and Hass Company, Philadelphia, Pa.). The reaction was conducted at a pressure of about 10 mmHg and at a maintained temperature of about 120° C. for 5 hours. Water collection during the 5 hour reaction period recovered about 200 g of produced water, indicating completion of the reaction. The resulting mixture was filtered to remove the catalyst. Upon removal of the catalyst, about 725.5 g of dark, highly viscous crude product was recovered.

The crude product was distilled utilizing a batch distillation apparatus. A first portion of isosorbide distilled out over a temperature between about 145° C. and 150° C. The first portion was a clear, nearly colorless oil which upon cooling formed white crystals. The crystallized first portion had an isosorbide purity of greater than 99% and a product yield of 61% relative to the initial amount of sorbitol.

After distillation recovery of the first portion of isosorbide, a second portion of isosorbide was recovered by increasing the distillation temperature. The second portion distilled out over a temperature of from about 170° C. to about 175° C. The second portion was recovered as a light yellow oil which solidified upon cooling. The resulting solid was washed with acetone. The washing removed the yellow color and resulted in a product having an isosorbide purity of about 96%. After washing, the isosorbide product yield of the second portion was about 10% relative to the initial sorbitol. The second portion was recrystallized from acetone to produce an isosorbide product of 99.5% purity.

Based upon the above results, a total isosorbide product yield of 71% was achieved utilizing the 2 step distillation technique. This yield can be increased by washing the catalyst (with acetone or ethanol for example) after the filtration step to recover any retained isosorbide product.

Although the invention is discussed as producing a final dianhydro product, the invention contemplates utilization of the methods presented for production of one or more monocyclic anhydrosugar alcohols. The monocyclic product(s) can optionally be isolated and/or purified. Additionally, the monocyclic products can be utilized to form other useful compounds.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A method of producing a dianhydrosugar alcohol comprising:
   in a first reactor, reacting a polyol in the presence of a first catalyst to form a monocyclic sugar, the first catalyst being a solid acid catalyst selected from the group consisting of a heteropoly acid, an anion exchange resin, an acidic clay, a molecular sieve material and a sulfated zirconia;
   transferring the monocyclic sugar to a second reactor; and
   in a second reactor, converting the monocyclic sugar to a dianhydrosugar alcohol in the presence of a second catalyst selected from the group consisting of sulfuric acid, phosphoric acid, hydrochloric acid and p-toluenesulfonic acid; the reacting a polyol being conducted at a first temperature and the converting being conducted at a second temperature that is higher than the first temperature.

2. The method of claim 1 wherein the dianhydrosugar alcohol is isosorbide.

3. The method of claim 1 wherein the first temperature is from about 90° C. to about 120° C.

4. The method of claim 3 wherein the first temperature is less than or equal to 110° C.

5. The method of claim 1 wherein the second temperature is from about 120° C. to about 200° C.

6. The method of claim 5 wherein the second temperature is less than or equal to about 140° C.

7. The method of claim 1 wherein the monocyclic sugar is a first monocyclic sugar, wherein the dianhydrosugar alcohol is a first dianhydrosugar alcohol and further comprising:
   simultaneous to forming the first monocyclic sugar, forming a second monocyclic sugar from the polyol in the first reactor; and
   converting the second monocyclic sugar to a second dianhydrosugar alcohol in the second reactor.

8. The method of claim 7 wherein the first dianhydrosugar alcohol and the second dianhydrosugar alcohol are the same.

9. The method of claim 7 wherein at least one additional monocyclic sugar is formed from the polyol in the first reactor, the at least one additional monocyclic sugar being formed at a ratio of less than about 8:1 relative to a total amount of first and second monocyclic sugars.

10. The method of claim 9 wherein the at least one additional monocyclic sugar is introduced into the second reactor and retains monocyclic form in the presence of the second catalyst.

11. The method of claim 1 wherein the transferring the monocyclic sugar occurs when an initial amount of the polyol has been depleted by from about 90% to about 95%.

12. A method of forming isosorbide, comprising:
   conducting an initial reaction within a first vessel, the initial reaction being conducted at a first temperature in the presence of a solid acid catalyst selected from the group consisting of a heteropoly acid, an anion exchange resin, an acidic clay, a molecular sieve material and a sulfated zirconia, and comprising reacting sorbitol to produce initial products comprising:
- a first intermediate and a second intermediate, the first intermediate being 1,4-sorbitan and the second intermediate being 3,6-sorbitan, and
- a first byproduct and a second byproduct, the first byproduct being 2,5-iditan and the second byproduct being 2,5-mannitan;

transferring the first and second intermediates to a second vessel; and within the second vessel and at a second temperature greater than the first temperature, converting the first and second intermediates to isosorbide in the presence of a second catalyst selected from the group consisting of sulfuric acid, phosphoric acid, hydrochloric acid and p-toluenesulfonic acid.

13. The method of claim 12 further comprising, prior to the initial reaction, removing at least some of any water present with the initial compound.

14. The method of claim 12 further comprising providing $H_2$ to the second reaction vessel during the converting.

15. The method of claim 14 wherein the converting is performed in the presence of a catalyst comprising metal on carbon.

16. The method of claim 12 further comprising performing a water removal step after the conducting the initial reaction and prior to the converting.

17. The method of claim 12 further comprising while conducting the initial reaction, removing at least some of any water generated during the initial reaction.

18. The method of claim 12 further comprising while converting the first and second intermediates, removing at least some of any water generated during the converting.

19. The method of claim 12 wherein the first temperature is from about 90° C. to about 120° C.

20. The method of claim 12 further comprising:
- collecting from the second vessel a composition comprising the isosorbide; and
- at least partially purifying the isosorbide.

21. The method of claim 20 wherein the at least partially purifying comprises at least one of crystallization, washing, distillation, and recrystallization.

22. The method of claim 20 wherein the at least partially purifying comprises a two step distillation procedure wherein a first step distillation is conducted at a first distillation temperature and a second step distillation is conducted at a second distillation temperature, the second distillation temperature being higher than the first distillation temperature.

23. The method of claim 22 wherein the first distillation temperature is from about 145° C. to about 155° C.

24. The method of claim 22 wherein the second distillation temperature is from about 170° C. to about 175° C.

* * * * *

UNITED STATES PATENT AND TRADEMARK OFFICE
CERTIFICATE OF CORRECTION

| | | |
|---|---|---|
| PATENT NO. | : 7,649,099 B2 | Page 1 of 1 |
| APPLICATION NO. | : 11/341961 | |
| DATED | : January 19, 2010 | |
| INVENTOR(S) | : Holladay et al. | |

It is certified that error appears in the above-identified patent and that said Letters Patent is hereby corrected as shown below:

Title Page, should read (*) Notice: Subject to any disclaimers, term of this patent is extended or adjusted under 35 U.S.C. 154(b) by 550 days.

Col. 5, Line 56 – Replace "step 300" with --step 310--.

Col. 10, Line 28 Claim 1 – Replace "a polyol" with --the polyol--.

Signed and Sealed this

Third Day of August, 2010

David J. Kappos
*Director of the United States Patent and Trademark Office*